(12) United States Patent
Chen et al.

(10) Patent No.: US 11,976,124 B2
(45) Date of Patent: May 7, 2024

(54) MONOCLONAL ANTIBODIES ACTIVATING CD40 AND USES THEREOF

(71) Applicant: ABVISION, INC., Milpitas, CA (US)

(72) Inventors: Chang-Hsin Chen, San Jose, CA (US); Gloria Zhang, Reno, NV (US); Guochen Yan, Reno, NV (US); Cheng-Chi Chao, Reno, CA (US)

(73) Assignee: ABVISION, INC., San Jose, CA (US)

( * ) Notice: Subject to any disclaimer, the term of this patent is extended or adjusted under 35 U.S.C. 154(b) by 805 days.

(21) Appl. No.: 17/132,324

(22) Filed: Dec. 23, 2020

(65) Prior Publication Data

US 2021/0115149 A1 Apr. 22, 2021

Related U.S. Application Data

(63) Continuation of application No. 16/409,201, filed on May 10, 2019, now abandoned.

(60) Provisional application No. 62/669,863, filed on May 10, 2018.

(51) Int. Cl.
| | |
|---|---|
| A61K 39/395 | (2006.01) |
| A61K 39/00 | (2006.01) |
| A61K 47/68 | (2017.01) |
| C07K 16/28 | (2006.01) |
| G01N 33/574 | (2006.01) |

(52) U.S. Cl.
CPC ...... *C07K 16/2878* (2013.01); *A61K 47/6851* (2017.08); *C07K 2317/24* (2013.01); *C07K 2317/54* (2013.01); *C07K 2317/55* (2013.01); *C07K 2317/56* (2013.01); *C07K 2317/75* (2013.01)

(58) Field of Classification Search
CPC ............ C07K 16/2878; C07K 2317/24; C07K 2317/75
See application file for complete search history.

(56) References Cited

U.S. PATENT DOCUMENTS

| | | | | |
|---|---|---|---|---|
| 2009/0280128 A1* | 11/2009 | Kamogawa | .............. | C12N 5/00 435/69.6 |
| 2012/0177664 A1* | 7/2012 | Yokoseki | .............. | C07K 16/18 530/387.3 |
| 2016/0251419 A1* | 9/2016 | Graham | ................. | C07K 16/18 424/9.1 |
| 2020/0181249 A1* | 6/2020 | Curtis | ..................... | A61P 13/12 |
| 2020/0222518 A1* | 7/2020 | Xin | ......................... | C07K 16/20 |
| 2020/0317758 A1* | 10/2020 | Torres | ................ | C07K 16/1271 |

OTHER PUBLICATIONS

P.E. Johnson et al. (2015). Clinical and Biological Effects of an Agonist Anti-CD40 Antibody: A Cancer Research UK Phase I Study. Clinical Cancer Research 21(6): 1321-1328. (Year: 2015).*
J.E. Grilley-Olson et al. (2018). "SEA-CD40, a non-fucosylated CD40 agonist: Interim results from a phase 1 study in advanced solid tumors." Meeting Abstract in Journal of Clinical Oncology 36(15 suppl). (Year: 2018).*
R.H. Vonderheide. (2020). "CD40 Agonist Antibodies in Cancer Immunotherapy." Annual Review of Medicine 71: 47-58. (Year: 2020).*
D.M. Richards et al. (2020). "Concepts for agonistic targeting of CD40 in immuno-oncology." Human Vaccines & Immunotherapeutics 16(2): 377-387. (Year: 2020).*
K. Enell Smith et al. (2021). "Rationale and clinical development of CD40 agonistic antibodies for cancer immunotherapy." Expert Opinion on Biological Therapy 21(12): 1635-1646/ (Year: 2021).*
D. Djureinovic et al. (2021). "Agonistic CD40 antibodies in cancer treatment." Cancers 13, 1302. (Year: 2021).*
E.L. Filbert et al. (2021). "APX005M, a CD40 agonist antibody with unique epitope specificity and Fc receptor binding profile for optimal therapeutic application." Cancer Immunology, Immunotherapy 70: 1853-1865. (Year: 2021).*

* cited by examiner

*Primary Examiner* — Julie Wu
*Assistant Examiner* — Elizabeth A Shupe
(74) *Attorney, Agent, or Firm* — Yong Chen; Lin Sun-Hoffman; Liu Chen & Hoffman LLP

(57) ABSTRACT

The present disclosure provides isolated monoclonal antibodies or an antigen-binding portion thereof that specifically bind to CD40 preferably human CD40 with high affinity, and that function as CD40 agonists. The disclosed invention also relates to antibodies that are chimeric, humanized, bispecific, derivatized, single chain antibodies or portions of fusion proteins. Nucleic acid molecules encoding the antibodies of the disclosed invention, hybridoma, and methods for expressing the antibodies of the disclosed invention are also provided. Pharmaceutical compositions comprising the antibodies of the disclosed invention are also provided. This disclosure also provides methods for regulating humoral and cellular immune responses, as well as methods for treating cancer using an anti-CD40 agonist antibody of the disclosed invention.

19 Claims, 2 Drawing Sheets
Specification includes a Sequence Listing.

Heavy chain sequence (V domain)

```
          <---------------------FR1-IMGT-----------------------><---CDR1-IM
         Q V Q L Q Q S G A E L M K P G A S V R I S C K A T G Y T F S
Query_1 88 CAGGTTCAGCTGCAGCAGTCTGGAGCTGAACTGATGAAGCCTGGGGCCTCAGTGAAGATATCCTGCAAGGCTACTGGCTACACAATTCAGT GT------><-----------FR2-IMGT--------------><----CDR2-IMGT----><-------
         G Y W I E W I K Q R P G H V L E W I G E I L P G S G S A N Y
Query_1 178 GGCTACTGGATAGAGTGGATAAAGCAGAGGCCTGGACATGTCCTTGAGTGGATTGGAGAGATTTTACCTGGAAGTGGTAGTGCTAACTAC --------------FR3-IMGT----------------------------><---
         N E K F K G K A T F T A D T S S N T A Y M Q L T S L T S E D
Query_1 268 AATGAAAAGTTCAAGGGCAAGGCCACATTCACTGCAGATACATCCTCCAACACAGCCTACATGCAACTCACCAGCCTGACATCTGAGGAC ----CDR3-IMGT------>
         S A V Y Y C A R L R Y Y G S S P W F A W G Q G T L V T V S
Query_1 358 TCTGCCGTCTATTACTGTGCAAGATAAGGTACGGTACTACGGTAGCAGCCCCTGGTTTGCTTACTGGGGCCAAGGGACTCTGGTCACTGTCTCT A
Query_1 448 GCA 450
```

Light chain sequence (V domain)

```
          <---------------------FR1-IMGT----------------------->
         D I V M S Q S P S S L A V S V G E K V T M S C K S S Q S L L
Query_1 758 GACATTGTGATGTCACAGTCTCCATCCTCCCTAGCTGTGTCAGTGGGAGAAGGTTACTATGAGCTGCAAGTCCAGTCAGAGCCTTTTA --------><----CDR1-IMGT---><---------FR2-IMGT---------><<CDR2-IM><----
         Y S S N Q K N Y L A W Y Q Q K P G Q S P K L L I Y W A S T R
Query_1 848 TATAGTAGCAATCAAAAGAACTACTTGGCTTGGTACCAGCAGAAACCAGGGCAGTCTCCTAAACTGCTGATTTACTGGGCATCCACTAGG -------------FR3-IMGT------------------------>
         E S G V P D R F T G S G S G T D F T L T I S S V K A E D L A
Query_1 938 GAATCTGGGGTCCCTGATCGCTTCACAGGCAGTGGATCTGGGACAGATTTCACTCTCACCATCAGCAGTGTGAAGGCTGAAGACCTGGCA <---CDR3-IMGT------>
         L Y Y C Q Q H Y S F P L T F G G G T K L E I K
Query_1 1028 CTTTATTACTGTCAGCAATATAGTAAGTTACCGCTCACGTTCGGTGCTGGGACCAAGCTGGAAATAAAA 1096
```

FIG. 1

MONOCLONAL ANTIBODIES ACTIVATING CD40 AND USES THEREOF

BACKGROUND OF THE INVENTION

The CD40 antigen is a 50 kDa cell surface glycoprotein which belongs to the Tumor Necrosis Factor Receptor (TNF-R) family. (Stamenkovic et al., *EMBO J.* 8: 1403-10 (1989).) CD40 is expressed on B lymphocytes, dendritic cells, macrophages and other cell types and is important for regulation of cell differentiation to effector cells that promote immune responses to antigens. CD40 is expressed in all B-lymphomas and in 70% of all solid tumors. Although constitutively expressed, CD40 is up-regulated in antigen presenting cells by maturation signals, such as LPS, IL-1βp, IFN-γ and GM-CSF.

CD40 activation plays a critical role in regulating humoral and cellular immune responses. Antigen presentation without CD40 activation can lead to tolerance, while CD40 signaling can reverse such tolerance, enhance antigen presentation by all antigen presenting cells (APCs), lead to secretion of helper cytokines and chemokines, increase co-stimulatory molecule expression and signaling, and stimulate the cytolytic activity of immune cells. CD40 plays a critical role in B cell proliferation, maturation and class switching. (Foy T. M. et al., *Ann. Rev.* of Immunol. 14:591-617 (1996).) CD40 engagement by CD40L leads to the association of the CD40 cytoplasmic domain with TRAFs (TNF-R associated factors). (Lee H. H. et al., *Proc. Natl. Acad. Sci. USA* 96:1421-6 (1999). In addition to enhancement of cellular and immune function, the effects of CD40 activation include: Cell recruitment and differentiation by chemokines and cytokines; activation of monocytes; increased cytolytic activity of cytolytic T lymphocyte (CTL) and natural killer (NK) cells; induction of apoptosis in CD40 positive tumors; enhancement of immunogenicity of CD40 positive tumors; and tumor-specific antibody production.

CD40 activation relies on CD40 ligand (CD40L or CD154). However, the majority of CD40L is expressed on CD4+ T cells or platelets, which are not easy to manipulate under in vivo physiological conditions. The disclosed antibodies targeting CD40 can bypass the need of CD40L for activation. The high stability of antibodies possesses numerous advantages for use in potential therapeutics.

There exists a need in the art for antibodies or an antigen-binding portion thereof, including chimeric and humanized antibodies, that bind CD40 and cause activation of CD40 downstream signaling, and that can have applications in the treatment of cancer and targeted vaccine adjuvants.

SUMMARY OF THE INVENTION

The present disclosure provides an isolated monoclonal antibody, or an antigen-binding portion thereof, that specifically binds to and activates human CD40. The newly developed antibodies have a high affinity and can target different epitopes on human CD40, compared to published antibodies.

In one aspect, the disclosed invention pertains to a monoclonal antibody, or an antigen-binding portion thereof that specifically binds to and activates human CD40, wherein said antibody or portion thereof comprises heavy chains: CDR1 amino acid sequence, CDR2 amino acid sequence, and CDR3 amino acid sequence, respectively, of amino acid residues 26-33, 51-58, and 97-111 of SEQ ID NO:1; and light chains: CDR1 amino acid sequence, CDR2 amino acid sequence, and CDR3 amino acid sequence, respectively, of amino acid residues 27-38, 56-58, and 95-103 of SEQ ID NO:2. In another aspect, the disclosed invention pertains to a monoclonal antibody, or an antigen-binding portion thereof that specifically binds to and activates human CD40, wherein said antibody or portion thereof comprises heavy chains: CDR1 amino acid sequence, CDR2 amino acid sequence, and CDR3 amino acid sequence, respectively, of amino acid residues 26-33, 51-58, and 97-104 of SEQ ID NO:10; and light chains: CDR1 amino acid sequence, CDR2 amino acid sequence, and CDR3 amino acid sequence, respectively, of amino acid residues 27-32, 50-52, and 89-97 of SEQ ID NO:11. In some embodiments, the monoclonal antibody, or said antigen-binding portion thereof stimulates an anti-tumor immune response. In some embodiments, the monoclonal antibody can be a chimeric antibody or a humanized antibody. In another aspect, anti-CD40 agonist antibodies can have a significant higher half-life in serum than CD40L.

In another aspect, the disclosed invention pertains to an isolated monoclonal antibody or an antigen-binding portion thereof that specifically binds to and activates human CD40, wherein said antibody comprises: a heavy chain variable domain comprising SEQ ID NO:1 and a light chain variable domain comprising SEQ ID NO:2. In another aspect, the disclosed invention pertains to an isolated monoclonal antibody or an antigen-binding portion thereof that specifically binds to and activates human CD40, wherein said antibody comprises: a heavy chain variable domain comprising SEQ ID NO:10 and a light chain variable domain comprising SEQ ID NO:11. In some embodiments, the monoclonal antibody, or an antigen-binding portion thereof stimulates an anti-tumor immune response. In some embodiments, the monoclonal antibody can be a chimeric antibody or a humanized antibody.

The antibodies of the disclosed invention can be further engineered into formats suitable for human therapeutics by modifications that minimize immunogenicity. Suitable antibodies include, but are not limited to chimeric antibodies and humanized antibodies. The affinity, stability and specificity of the disclosed antibodies can also be further optimized by techniques known to one of skill in the art such as light-chain shuffling. Other formats can involve oligomerization, drug conjugation and fusion of the disclosed antibodies with other functional proteins.

In another aspect, the antibodies of the disclosed invention can be, for example, full-length antibodies, for example of an IgG1, IgG2, IgG3, or IgG4 isotype. Alternatively, the disclosed antibodies can be antibody fragments, such as Fab, Fab' and F(ab')₂ fragments, diabody, triabody, tetrabody, single-chain variable region fragment (scFv), disulfide-stabilized variable region fragment (dsFv), and half antibodies. Alternatively, the disclosed antibodies can be bispecific antibodies.

In another aspect, this disclosure provides an isolated monoclonal antibody, or antigen binding portion thereof comprising: (a) a heavy chain variable region CDR1 comprising SEQ ID NO:3; (b) a heavy chain variable region CDR2 comprising SEQ ID NO:4; (c) a heavy chain variable region CDR3 comprising SEQ ID NO:5; (d) a light chain variable region CDR1 comprising SEQ ID NO:6; (e) a light chain variable region CDR2 comprising Trp-Ala-Ser; and (f) a light chain variable region CDR3 comprising SEQ ID NO:7; wherein said antibody specifically binds to and activates human CD40.

In another aspect, this disclosure provides an isolated monoclonal antibody, or antigen binding portion thereof comprising: (a) a heavy chain variable region CDR1 comprising SEQ ID NO:12; (b) a heavy chain variable region CDR2 comprising SEQ ID NO:13; (c) a heavy chain variable region CDR3 comprising SEQ ID NO:14; (d) a light chain variable region CDR1 comprising SEQ ID NO:15; (e) a light chain variable region CDR2 comprising Trp-Thr-Ser; and (f) a light chain variable region CDR3 comprising SEQ ID NO:16; wherein said antibody specifically binds to and activates human CD40.

In another aspect, a pharmaceutical composition comprising isolated monoclonal antibody, or antigen-binding portion thereof and a pharmaceutically acceptable carrier are also provided.

In another aspect, the disclosed invention pertains to methods of stimulating immune responses using the anti-CD40 agonist antibodies of the disclosed invention. For example, in one embodiment, the disclosed invention provides a method for treating a subject in need thereof, wherein said response is indicated by activation of antigen presenting cells, comprising the step of administering to the subject an effective amount of the antibody or antigen-binding portion of the disclosed invention.

In another aspect, the disclosed invention provides a method for treating cancer in a human comprising the step of administering to the human the antibody or antigen-binding portion of the disclosed invention in an amount effective to treat said cancer.

In yet another aspect, the disclosed invention pertains to a monoclonal antibody or an antigen-binding portion thereof that specifically binds to and activates human CD40, wherein said antibody comprises: a heavy chain variable domain amino acid sequence encoded by a nucleic acid sequence comprising SEQ ID NO:8 or 17 and a light chain variable domain amino acid sequence encoded by a nucleic acid sequence comprising SEQ ID NOs:9 or 18. In yet another aspect, the invention also provides nucleic acid molecules encoding the heavy and/or light chain, or antigen-binding portions thereof, of an anti-CD40 antibody.

Other features and advantages of the instant disclosure will be apparent from the following detailed description and examples, which should not be construed as limiting. The contents of all references, GenBank entries, patents and published patent applications cited throughout this application are expressly incorporated herein by reference.

BRIEF DESCRIPTION OF THE DRAWINGS

FIG. 1 illustrates antibody heavy chain and light chain variable domain protein sequences and corresponding DNA sequences of the disclosed invention encoding the heavy chain and light chain variable domains of anti-human CD40 agonistic mAb (clone #1E10-H2), in one embodiment. Heavy chain V domain of 1E10-H2 is SEQ ID NO:1 and nucleic acid sequence is SEQ ID NO:8, Light chain V domain of 1E10-H2 is SEQ ID NO:2 and nucleic acid sequence is SEQ ID NO:9.

DETAILED DESCRIPTION OF THE INVENTION

Figure 2:
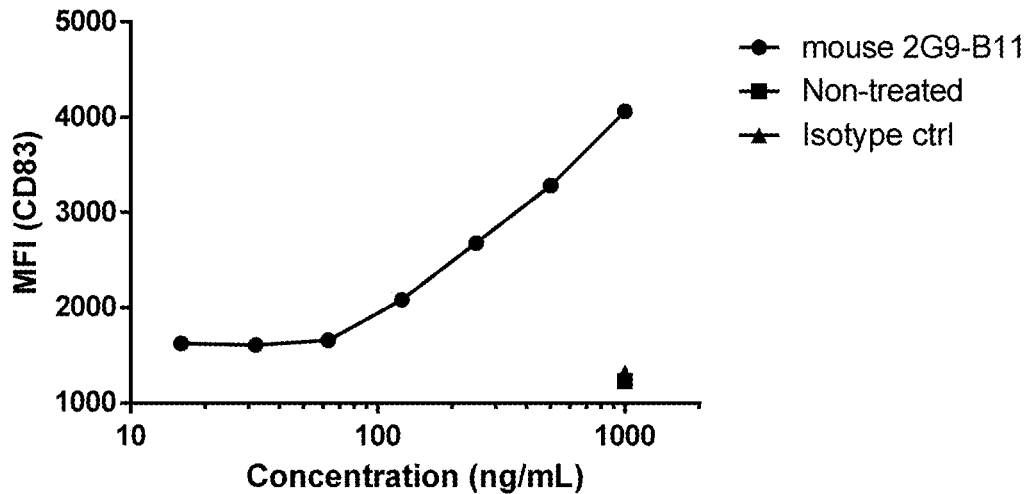
FIG. 2 illustrates that anti-human CD40 antibodies of the present disclosure induced activation marker CD83 expression from human primary monocyte-derived dendritic cells in a co-cultured reaction assay. Isotype antibody control: mouse anti-BrdU (isotype: IgG1); mouse anti-CD40 antibodies (isotype: IgG1): clone #2G9-B11.

The present disclosure relates to an isolated monoclonal antibody which binds to CD40 and acts as a CD40 agonist. In certain embodiments, the antibodies of the disclosed invention are derived from identified heavy and light chain germline sequences and/or comprise identified structural features such as CDR regions comprising identified amino acid sequences. This disclosure provides isolated antibodies, methods of making such antibodies and antigen-binding portions thereof of the disclosed invention. This disclosure also relates to methods of using the antibodies, such as using the anti-CD40 agonist antibodies of the disclosed invention to stimulate immune responses, alone or in combination with other immunostimulatory antibodies. Accordingly, also provided are methods of using the anti-CD40 agonist antibodies of the disclosed invention for example, including but not limited to, treating cancer in a human.

In order that the present disclosure may be more readily understood, certain terms are first defined. Additional definitions are set forth throughout the detailed description.

An "activating antibody" (also referred to herein as an "agonist antibody") as used herein can refer to an antibody that increases one or more CD40 activities by at least about 20% when added to a cell, tissue or organism expressing CD40. In some embodiments, the antibody activates CD40 activity by at least about 40%, about 50%, about 60%, about 70%, about 80%, and about 85%. In some embodiments, the activating antibody is added in the presence of CD40L. In some embodiments, the activity of the activating antibody is measured using a whole blood surface molecule upregulation assay. In another embodiment, the activity of the activating antibody is measured using a dendritic cell assay to measure IL-12 release. In another embodiment the activity of the activating antibody is measured using an in vivo tumor model.

The term "epitope" as used herein can include any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the equilibrium dissociation constant is ≤1 µM, preferably ≤100 nM and most preferably ≤10 nM.

The term "immune response" as used herein can refer to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from an organism of invading pathogens, cells or tissues infected with pathogens, cancerous cells, or, in cases of autoimmunity or pathological inflammation, normal organismal cells or tissues.

An "antigen-specific T cell response" as used herein can refer to responses by a T cell that result from stimulation of the T cell with the antigen for which the T cell is specific. Non-limiting examples of responses by a T cell upon antigen-specific stimulation include, but are not limited to, proliferation and cytokine production (e.g., IL-2 production).

The term "antibody" as used herein can include whole antibodies, F(ab')2 fragment, diabody, triabody, tetrabody, bispecific antibody, monomeric antibodies and any antigen binding fragment (i.e., "antigen-binding portion") or single-chain variable region fragment (scFv), or disulfide-stabilized variable region fragment (dsFv) thereof. Whole antibodies are glycoproteins comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region (CL). The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, can refer to one or more fragments of an antibody that retain the ability to specifically bind to an antigen (e.g., a CD40 protein). It has been shown that the antigen-binding function of an antibody can be performed by fragments of a full-length antibody. Examples of binding fragments encompassed within the term "antigen binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the VH and CH1 domains; (v) a Fv fragment consisting of the VL and VH domains of a single arm of an antibody; (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains. Furthermore, although the two domains of the Fv fragment, VL and VH are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as intact antibodies.

An "isolated antibody", as used herein, can refer to an antibody that is substantially free of other antibodies having different antigenic specificities (e.g., an isolated antibody that specifically binds a CD40 protein can be substantially free of antibodies that specifically bind antigens other than CD40 proteins). An isolated antibody that specifically binds a human CD40 protein can, however, have cross-reactivity to other antigens, such as CD40 proteins from other species. Moreover, an isolated antibody can be substantially free of other cellular material and/or chemicals.

Anti-CD40 agonist antibody-producing cells, e.g., hybridomas, can be selected, cloned and further screened for desirable characteristics, including robust growth, high antibody production and desirable antibody characteristics, as further discussed below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

The terms "monoclonal antibody" or "monoclonal antibody composition" as used herein can refer to a preparation of antibody molecules of single molecular composition. A monoclonal antibody composition displays a single binding specificity and affinity for a particular epitope.

The term "recombinant human antibody", as used herein, can refer to all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" can refer to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "humanized antibody" can refer to antibodies in which CDR sequences derived from the germline of another mammalian species, such as a mouse, have been grafted onto human framework sequences. Additional framework region modifications can be made within the human framework sequences.

The term "chimeric antibody" can refer to antibodies in which the variable region sequences can be derived from one species and the constant region sequences can be derived from another species, such as an antibody in which the variable region sequences can be derived from a mouse antibody and the constant region sequences can be derived from a human antibody.

The term "surface plasmon resonance", as used herein, can refer to an optical phenomenon that allows for the analysis of real-time biospecific interactions by detection of alterations in protein concentrations within a biosensor matrix, for example using the BIAcore™ system (Pharmacia Biosensor AB, Uppsala, Sweden and Piscataway, N.J.). For further descriptions, see Jonsson U. et al., *Ann. Biol. Clin.* 51:19-26 (1993); Jonsson U. et al., *Biotechniques* 11:620-627 (1991); Jonsson B. et al., *J. Mal. Recognit.* 8:125-131 (1995); and Johnsson B. et al., *Anal. Biochem.* 198:268-277 (1991).

The term "$K_D$" can refer to the equilibrium dissociation constant of a particular antibody-antigen interaction.

As used herein, an antibody that "specifically binds human CD40" can refer to an antibody that binds to a human CD40 protein (and possibly a CD40 protein from one or more non-human species) but does not substantially bind to non-CD40 proteins. Preferably, the antibody binds to a human CD40 protein with "high affinity," namely with a $EC_{50}$ of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$M or less or even more preferably $1\times10^{-9}$ M or less.

The term "does not substantially bind" to a protein or cells, as used herein, can mean that it cannot bind or does not bind with a high affinity to the protein or cells, i.e., binds to the protein or cells with an $EC_{50}$ of $2\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "high affinity" for an IgG antibody can refer to an antibody having an $EC_{50}$ of $1\times10^{-6}$ M or less, more preferably $1\times10^{-7}$ M or less, even more preferably $1\times10^{-8}$ M or less, even more preferably $1\times10^{-9}$ M or less, even more preferably $1\times10^{-10}$ M or less for a target antigen. However, "high affinity" binding can vary for other antibody isotypes.

The term "subject" can refer to any human or non-human animal. The term "nonhuman animal" includes all vertebrates, e.g., mammals and non-mammals, such as nonhuman primates, sheep, dogs, cats, cows, horses, chickens, rabbits, mice, rats, amphibians, and reptiles, although mammals are preferred, such as non-human primates, sheep, dogs, cats, cows and horses.

The binding of an antibody of the disclosed invention to CD40 can be assessed using one or more techniques well established in the art. For example, in a preferred embodiment, an antibody can be tested by ELISA assays, for example using a recombinant CD40 protein. Still other suitable binding assays include but are not limited to a flow cytometry assay in which the antibody is reacted with a cell line that expresses human CD40, such as CHO cells that have been transfected to express CD40 (e.g., human CD40) on their cell surface. Additionally or alternatively, the binding of the antibody, including the binding kinetics (e.g., $K_D$ value) can be tested in BIAcore binding assays and the like.

Preferably, an antibody of the disclosed invention binds to a CD40 protein with an $EC_{50}$ of $5\times10^{-8}$ M or less, binds to a CD40 protein with a $EC_{50}$ of $2\times10^{-8}$ M or less, binds to a CD40 protein with a $EC_{50}$ of $5\times10^{-9}$ M or less, binds to a CD40 protein with a $EC_{50}$ of $4\times10^{-9}$ M or less, binds to a CD40 protein with a $EC_{50}$ of $3\times10^{-9}$ M or less, binds to a CD40 protein with a $EC_{50}$ of $2\times10^{-9}$ M or less, binds to a CD40 protein with a $EC_{50}$ of $1\times10^{-9}$ M or less.

Antibodies can be isolated and structurally characterized as described in Example 1. The VH amino acid sequence of clone #1E10-H2 is shown in SEQ ID NO:1. The VL amino acid sequence of clone #1E10-H2 is shown in SEQ ID NO:2. The VH amino acid sequence of clone #2G9-B11 is shown in SEQ ID NO:10. The VL amino acid sequence of clone #2G9-B11 is shown in SEQ ID NO:11.

Accordingly, in one aspect, this disclosure provides an isolated monoclonal antibody, or antigen-binding portion thereof comprising: (a) a heavy chain variable region comprising an amino acid sequence comprising SEQ ID NO:1; and (b) a light chain variable region comprising an amino acid sequence comprising SEQ ID NO:2; wherein the antibody specifically binds and activates human CD40.

In another aspect, this disclosure provides an isolated monoclonal antibody, or antigen-binding portion thereof comprising: (a) a heavy chain variable region comprising an amino acid sequence comprising SEQ ID NO:10; and (b) a light chain variable region comprising an amino acid sequence comprising SEQ ID NO:11; wherein the antibody specifically binds and activates human CD40. In some embodiments, the monoclonal antibody, or an antigen-binding portion thereof stimulates an anti-tumor immune response. In some embodiments, the monoclonal antibody can be a chimeric antibody.

In another aspect, this disclosure provides antibodies that comprise the heavy chain and light chain CDR1, CDR2 and CDR3 of clone #1E10-H2. The amino acid sequence of the VH CDR1 of clone #1E10-H2 is shown in SEQ ID NO:3. The amino acid sequence of the VH CDR2 of clone #1E10-H2 is shown in SEQ ID NO:4. The amino acid sequence of the VH CDR3 of clone #1E10-H2 is shown in SEQ ID NO:5. The amino acid sequences of the VL CDR1 of clone #1E10-H2 is shown in SEQ ID NO:6. The amino acid sequences of the VL CDR2s of clone #1E10-H2 is Trp-Ala-Ser. The amino acid sequences of the VL CDR3s of clone #1E10-H2 is shown in SEQ ID NO:7.

In another aspect, this disclosure provides antibodies that comprise the heavy chain and light chain CDR1, CDR2 and CDR3 of clone #2G9-B11. The amino acid sequence of the VH CDR1 of clone #2G9-B11 is shown in SEQ ID NO:12. The amino acid sequence of the VH CDR2 of clone #2G9-B11 is shown in SEQ ID NO:13. The amino acid sequence of the VH CDR3 of clone #2G9-B11 is shown in SEQ ID NO:14. The amino acid sequences of the VL CDR1 of clone #2G9-B11 is shown in SEQ ID NO:15. The amino acid sequences of the VL CDR2s of clone #2G9-B11 is Trp-Thr-Ser. The amino acid sequences of the VL CDR3s of clone #2G9-B11 is shown in SEQ ID NO:16. The CDR regions can be delineated using the Kabat system (Kabat et al. (1991) Sequences of Proteins of Immunological Interest, Fifth Edition, U.S. Department of Health and Human Services, NIH Publication No. 91-3242).

In another aspect, this disclosure provides polynucleotide sequences encoding the heavy chain and light chain variable domains of the monoclonal antibody clone #1E10-H2. In another aspect, this disclosure provides polynucleotide sequences encoding the heavy chain and light chain variable domains of the monoclonal antibody clone #2G9-B11.

Antibodies can be affinity matured by light-chain shuffling combined with or without random mutagenesis of its heavy chain variable domain and panning against CD40. The VL CDR1, CDR2 and CDR3 of the antibodies mentioned in this disclosed invention can be optimized with light-chain shuffling to create other anti-CD40 agonist binding molecules of the disclosed invention.

An antibody of the disclosed invention further can be prepared using an antibody having one or more of the VH and/or VL sequences disclosed herein as starting material to engineer a modified antibody, which modified antibody can have altered properties from the starting antibody. An antibody can be engineered by modifying one or more residues within one or both variable regions (i.e., VH and/or VL), for example within one or more CDR regions and/or within one or more framework regions. Additionally, or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs can be more diverse between individual antibodies than sequences outside of CDRs.

Because CDR sequences can be responsible for most antibody-antigen interactions, it can be possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) Nature 332:323-327; Jones et al. (1986) Nature 321: 522-525; Queen et al. (1989) Proc. Natl. Acad. See. U.S.A. 86: 10029-10033; U.S. Pat. Nos. 5,225, 539; 5,530,101; 5,585,089; 5,693,762 and 6,180,370.)

Accordingly, another embodiment of the disclosed invention pertains to an isolated monoclonal antibody, or antigen-binding portion thereof, comprising a heavy chain variable region comprising CDR1, CDR2, and CDR3 sequences comprising an amino acid sequence of SEQ ID NO:3, SEQ ID NO:4, and SEQ ID NO:5, respectively, and a light chain variable region a comprising CDR1, CDR2, and CDR3 sequences comprising an amino acid sequence of SEQ ID NO:6, Trp-Ala-Ser, and SEQ ID NO:7, respectively. Another embodiment of the disclosed invention pertains to an isolated monoclonal antibody, or antigen-binding portion thereof, comprising a heavy chain variable region comprising CDR1, CDR2, and CDR3 sequences comprising an amino acid sequence of SEQ ID NO:12, SEQ ID NO:13, and SEQ ID NO:14, respectively, and a light chain variable region a comprising CDR1, CDR2, and CDR3 sequences comprising an amino acid sequence of SEQ ID NO:15, Trp-Thr-Ser, and SEQ ID NO:16, respectively. Thus, such antibodies contain the VH and VL CDR sequences of monoclonal antibody 1E10-H2 or 2G9-B11 and can contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline VH Sequences Reveals about Fifty Groups of VH Segments with Different Hypervariable Loops" J. Mol. Biol. 227:776-798; and Cox et al. (1994) "A Directory of Human Germ-line VH Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the GenBank database. For example, the following heavy chain germline sequences found in the HCo7 HuMAb mouse are available in the accompanying GenBankAccession NOS.:1-69 (NG_0010109, NT_024637 & BC070333), 3-33 (NG_0010109 & NT_024637) and 3-7 (NG_0010109 & NT_024637). As another example, the following heavy chain germline sequences found in the HCo12 HuMAb mouse are available in the accompanying GenBankAccession NOS.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art. The compositions and methods of the presently disclosed invention are not limited to variants of the exemplary sequences disclosed herein but include those having at least 90%, at least 95% and at least 99% sequence identity to an exemplary sequence disclosed herein.

A nucleic acid molecule encoding the heavy or entire light chain of an anti-CD40 agonist antibody or portions thereof can be isolated from any source that produces such an antibody. In various embodiments, the nucleic acid molecules are isolated from a B cell isolated from an animal immunized with CD40 or from an immortalized cell derived from such a B cell that expresses an anti-CD40 agonist antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In a preferred embodiment, the nucleic acid molecule is isolated from a hybridoma that has as one of its fusion partners a human immunoglobulin producing cell from a non-human transgenic animal. In another embodiment, the nucleic acid can be isolated from a non-human, non-transgenic animal. The nucleic acid molecules isolated from a non-human, nontransgenic animal may be used, e.g., for humanized antibodies.

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the disclosed invention also can be administered in combination therapy with, for example, another immunostimulatory agent, an anti-cancer agent, an antiviral agent, or a vaccine, such that the anti-CD40 agonist antibody enhances the immune response stimulated by the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: The Science and Practice of Pharmacy, 20th Ed. (Lippincott Williams & Wilkins 2003), the disclosure of which is incorporated herein by reference.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-CD40 agonist antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

In certain embodiments, an anti-CD40 agonist antibody of the disclosed invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-CD40 agonist antibodies can be incorporated with excipients and used in the form of ingestible tablets, buccal tablets, troches, lozenge, capsules, elixirs, suspensions, syrups, wafers, and the like. To administer a compound of the disclosed invention by other than parenteral administration, it may be necessary to coat the compound with, or co-administer the compound with, a material to prevent its inactivation.

Additional active compounds also can be incorporated into the disclosed compositions. In certain embodiments, an anti-CD40 agonist antibody of the disclosed invention is co-formulated with and/or co-administered with one or more additional therapeutic agents. These agents include, without limitation, antibodies that bind other targets (e.g., antibodies that bind one or more growth factors or cytokines or their cell surface receptors, such as anti-CTL4-antibody), antineoplastic agents, antitumor agents, chemotherapeutic agents, peptide analogues that activate CD40, soluble CD40L, one or more chemical agents that activates CD40, and/or other agents known in the art that can enhance an immune response against tumor cells, e.g., IFN-1, IL-2, IL-8, IL-12, IL-15, IL-18, IL-23, IFN-y, and GM-CSF. Such combination therapies may require lower dosages of the anti-CD40 agonist antibody as well as the co-administered agents, thus avoiding possible toxicities or complications associated with the various monotherapies.

Agonist anti-CD40 antibodies of the disclosed invention and compositions comprising them also may be administered in combination with other therapeutic regimens, in particular in combination with radiation treatment.

The pharmaceutical compositions of the disclosed invention can include pharmaceutically acceptable salts. A "pharmaceutically acceptable salt" can refer to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the antibody can be administered as a sustained release formulation, in which case less frequent administration can be required.

An exemplary, non-limiting range for a therapeutically or prophylactically effective amount of an antibody or antibody portion of the disclosed invention is 0.025 to 50 mg/kg, more preferably 0.1 to 50 mg/kg, more preferably 0.1 to 25 mg/kg, 0.1 to 10 mg/kg and 0.1 to 3 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Bispecific antibodies or antigen-binding fragments can be produced by a variety of methods including fusion of hybridomas or linking of Fab' fragments. See, e.g., Songsivilai & Lachmarm, *Clin. Exp. Immunol.* 79: 315-321 (1990), Kos-telny et al., *J. Immunol.* 148:1547-1553 (1992). In addition, bispecific antibodies can be formed as "diabodies" or "Janusins." In some embodiments, the bispecific antibody binds to two different epitopes of CD40. In some embodiments, the bispecific antibody has a first heavy chain and a first light chain from monoclonal antibody 1E10-H2, and an additional antibody heavy chain and light chain. In some embodiments, the bispecific antibody has a first heavy chain and a first light chain from monoclonal antibody 2G9-B11, and an additional antibody heavy chain and light chain. In some embodiments, the additional light chain and heavy chain also are from one of the above-identified monoclonal antibodies, but can be different from the first heavy and light chains.

EXAMPLE 1

Immunization and Hybridoma Generation

Antibodies were created by electrofusion of human CD40-immunized mouse splenocytes (Balb/c strain) with SP2/0-A14 cells (ATCC) (Immunization procedure; dose, adjuvants, time course). Fused cells were seeded into 96-well plates and ELISA screening was conducted to identify wells that contain antibodies which interact with the human CD40 protein. Positive wells were further expanded and followed a limited dilution to isolate monoclonal hybridomas. Purified antibodies were used to test their ability to trigger CD40 signaling by an in-house created reporter system. Basically, an engineered 293T cell line was transduced to stably express the human CD40 protein. When testing the agonistic functions of CD40 antibodies, DNA plasmids of an NF-kB-driven luciferase reporter and Fc-gamma receptors were transiently transfected into established CD40-293T cells. Antibodies to be tested were added to the culture and incubated for 24 hours. Treated cells were harvested, lysed and analyzed on a plate reader for the activity of luciferase. Anti-human CD40 mAb clone #1E10-H2 and clone #2G9-B11 were tested binding to and activating human CD40. The sequences of the IgG heavy chain and light chain variable domains of anti-human CD40 agonistic mAb clone #1E10-H2 are shown in FIG. 1.

EXAMPLE 2

Anti-Human CD40 Antibody In-Vitro Assay

Frozen human primary monocytes (CD14+; negative selection) were differentiated into dendritic cells (DC) by culturing with rIL-4 and rGM-CSF for 5 days. $5\times10^5$ DCs were then co-cultured with $1\times10^5$ 293FT cells transient transfected with FcgR in 24-well plate, with serial diluted dosages of anti-CD40 2G9-B11 antibodies or fixed dosage of isotype control antibody, for additional 2 days. Cells were blocked with TruStain FcX antibody (BioLegend), followed by staining with PE/Cy5 anti-CD11c antibody (BioLegend, clone 3.9, mouse IgG1) and PE/Dazzle 594 anti-CD83 antibody (BioLegend, clone HB15e, mouse IgG1). Flow cytometry was performed using BD LSRII flow cytometer. Results are shown in FIG. 2, which demonstrate that anti-CD40 antibodies induced activation marker CD83 expression from human primary monocyte-derived dendritic cells in a co-cultured reaction assay.

EXAMPLE 3

Anti-Human CD40 Antibody In-Vitro Assay

Figure 3:
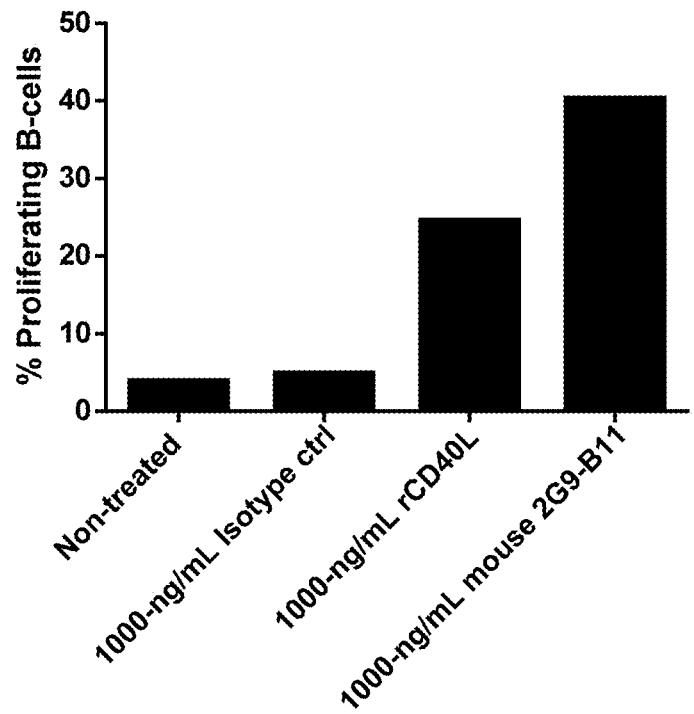
FIG. 3 illustrates that anti-human CD40 antibodies of the present disclosure induced human primary B-cells proliferation in a co-cultured reaction assay. Isotype antibody control: mouse anti-BrdU (isotype: IgG1); mouse anti-CD40 antibodies (isotype: IgG1): clone #2G9-B11.

Human primary B-cells isolated from human PBMC (Miltenyi Biotec, negative selection) were labeled with CFSE (BioLegend) and co-cultured with $1\times10^5$ 293FT cells transient transfected with FcgR in 24-well plate, with fixed dosage of antibodies, for 7 days. Cells were blocked with TruStain FcX antibody (BioLegend), followed by staining with APC goat anti-human IgG (H+L) antibody (Jackson ImmunoResearch). Flow cytometry was performed using BD LSRII flow cytometer. Results are shown in FIG. 3, which demonstrate that anti-CD40 antibodies induced human primary B-cells proliferation in a co-cultured reaction assay.

Although the above invention has been described in some detail by way of illustration and example for purposes of clarity of understanding, it is apparent to those skilled in the art that certain changes and modifications will be practiced. Therefore, the description and examples should not be construed as limiting the scope of the disclosed invention.

The disclosures of all publications, patents, patent applications and published patent applications referred to herein by an identifying citation are hereby incorporated herein by reference in their entirety. Websites references using "World-Wide-Web" at the beginning of the Uniform Resource Locator (URL) can be accessed by replacing "World-Wide-Web" with www.

What is claim is:

1. A monoclonal antibody, or an antigen-binding portion thereof comprising:
    (a) a heavy chain CDR1 amino acid sequence, CDR2 amino acid sequence, and CDR3 amino acid sequence, respectively, of amino acid residues 26-33, 51-58, and 97-104 of SEQ ID NO:10; and
    (b) a light chain CDR1 amino acid sequence, CDR2 amino acid sequence, and CDR3 amino acid sequence, respectively, of amino acid residues 27-32, 50-52, and 89-97 of SEQ ID NO:11, wherein said antibody or portion specifically binds to and activates human CD40.

2. The antibody or antigen-binding portion according to claim 1 that is a Fab fragment, an F(ab')₂ fragment, an Fv fragment, a single chain antibody, or a bispecific antibody.

3. A pharmaceutical composition comprising the antibody or antigen-binding portion-according to claim 1 and a pharmaceutically acceptable carrier.

4. A method of treating cancer in a human, comprising the step of administering to the human the antibody or antigen-binding portion according to claim 1 in an amount effective to treat said cancer.

5. A method of enhancing an immune response in a subject in need thereof, comprising the step of administering to the subject an effective amount of the antibody or antigen-binding portion according to claim 1, wherein said response is indicated by activation of antigen presenting cells.

6. The monoclonal antibody, or an antigen-binding portion thereof of claim 1, wherein the antibody stimulates an anti-tumor immune response.

7. A monoclonal antibody or an antigen-binding portion thereof comprising: a heavy chain variable domain comprising SEQ ID NO:10 and a light chain variable domain comprising SEQ ID NO:11, wherein the antibody specifically binds to and activates human CD40.

8. The antibody or antigen-binding portion according to claim 7 that is a Fab fragment, an F(ab')₂ fragment, an Fv fragment, a single chain antibody, or a bispecific antibody.

9. A pharmaceutical composition comprising the antibody or antigen-binding portion-according to claim 7 and a pharmaceutically acceptable carrier.

10. A method of treating cancer in a human, comprising the step of administering to the human the antibody or antigen-binding portion according to claim 7 in an amount effective to treat said cancer.

11. A method of enhancing an immune response in a subject in need thereof, comprising the step of administering to the subject an effective amount of the antibody or antigen-binding portion according to any claim 7, wherein said response is indicated by activation of antigen presenting cells in the subject in need thereof.

12. The antibody of claim 7, wherein the antibody stimulates an anti-tumor immune response.

13. An isolated monoclonal antibody, or antigen-binding portion thereof comprising
    (a) a heavy chain variable region CDR1 comprising SEQ ID NO:12;
    (b) a heavy chain variable region CDR2 comprising SEQ ID NO:13;
    (c) a heavy chain variable region CDR3 comprising SEQ ID NO:14;
    (d) a light chain variable region CDR1 comprising SEQ ID NO:15;
    (e) a light chain variable region CDR2 comprising Trp-Thr-Ser; and
    (f) a light chain variable region CDR3 comprising SEQ ID NO:16,
    wherein said antibody or portion specifically binds to and activates human CD40.

14. The antibody according to claim 1, that is an immunoglobulin G (IgG), an IgM, an IgE, an IgA or an IgD molecule, or is derived therefrom.

15. The monoclonal antibody according to claim 14, wherein said antibody is a chimeric antibody or humanized antibody.

16. The monoclonal antibody according to claim 14, wherein said antibody is an IgG1, IgG2, IgG3, or IgG4, or is derived therefrom.

17. The antibody according to claim 7, that is an immunoglobulin G (IgG), an IgM, an IgE, an IgA or an IgD molecule, or is derived therefrom.

18. The monoclonal antibody according to claim 17, wherein said antibody is an IgG1, IgG2, IgG3, or IgG4, or is derived therefrom.

19. The monoclonal antibody according to claim 17, wherein said antibody is a chimeric antibody or humanized antibody.

\* \* \* \* \*

SEQUENCE LISTING

<160> NUMBER OF SEQ ID NOS: 18

<210> SEQ ID NO 1
<211> LENGTH: 121
<212> TYPE: PRT
<213> ORGANISM: Artificial Sequence
<220> FEATURE:
<223> OTHER INFORMATION: monoclonal antibody

<400> SEQUENCE: 1

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Ile Lys Gln Arg Pro Gly His Val Leu Glu Trp Ile
        35                  40                  45

Gly Glu Ile Leu Pro Gly Ser Gly Ser Ala Asn Tyr Asn Glu Arg Phe
    50                  55                  60

Lys Gly Lys Ala Thr Phe Thr Ala Asp Thr Ser Ser Asn Thr Ala Tyr
65                  70                  75                  80

```
Met Gln Leu Thr Ser Leu Thr Ser Glu Asp Ser Ala Val Tyr Tyr Cys
                85                  90                  95

Ala Arg Leu Arg Tyr Tyr Gly Ser Ser Pro Trp Phe Ala Tyr Trp Gly
            100                 105                 110

Gln Gly Thr Leu Val Thr Val Ser Ala
        115                 120

<210> SEQ ID NO 2
<211> LENGTH: 113
<212> TYPE: PRT
<213> ORGANISM: Artificial Sequence
<220> FEATURE:
<223> OTHER INFORMATION: engineered mAb

<400> SEQUENCE: 2

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Leu Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 3
<211> LENGTH: 8
<212> TYPE: PRT
<213> ORGANISM: Artificial Sequence
<220> FEATURE:
<223> OTHER INFORMATION: engineered mAb

<400> SEQUENCE: 3

Gly Tyr Thr Phe Ser Ser Tyr Trp
1               5

<210> SEQ ID NO 4
<211> LENGTH: 8
<212> TYPE: PRT
<213> ORGANISM: Artificial Sequence
<220> FEATURE:
<223> OTHER INFORMATION: engineered mAb

<400> SEQUENCE: 4

Ile Leu Pro Gly Ser Gly Ser Ala
1               5

<210> SEQ ID NO 5
<211> LENGTH: 14
<212> TYPE: PRT
<213> ORGANISM: Artificial Sequence
<220> FEATURE:
<223> OTHER INFORMATION: engineered mAb

<400> SEQUENCE: 5

Ala Arg Leu Arg Tyr Tyr Gly Ser Ser Pro Trp Phe Ala Tyr
```

<210> SEQ ID NO 6
<211> LENGTH: 12
<212> TYPE: PRT
<213> ORGANISM: Artificial Sequence
<220> FEATURE:
<223> OTHER INFORMATION: engineered mAb

<400> SEQUENCE: 6

Gln Ser Leu Leu Tyr Ser Ser Asn Gln Lys Asn Tyr
1               5                   10

<210> SEQ ID NO 7
<211> LENGTH: 9
<212> TYPE: PRT
<213> ORGANISM: Artificial Sequence
<220> FEATURE:
<223> OTHER INFORMATION: engineered mAb

<400> SEQUENCE: 7

Gln Gln Tyr Tyr Ser Tyr Pro Tyr Thr
1               5

<210> SEQ ID NO 8
<211> LENGTH: 363
<212> TYPE: DNA
<213> ORGANISM: Artificial Sequence
<220> FEATURE:
<223> OTHER INFORMATION: monoclonal antibody plasmid

<400> SEQUENCE: 8

```
caggttcagc tgcagcagtc tggagctgaa ctgatgaagc ctggggcctc agtgaagata      60
tcctgcaagg ctactggcta cacattcagt agctactgga tagagtggat aaagcagagg     120
cctggacatg tccttgagtg gattggagag attttacctg gaagtggtag tgctaactac     180
aatgaaaggt tcaagggcaa ggccacattc actgcagata catcctccaa cacagcctac     240
atgcaactca ccagcctgac atctgaggac tctgccgtct attactgtgc aagattgagg     300
tactacggta gtagcccctg gtttgcttac tggggccaag ggactctggt cactgtctct     360
gca                                                                   363
```

<210> SEQ ID NO 9
<211> LENGTH: 339
<212> TYPE: DNA
<213> ORGANISM: Artificial Sequence
<220> FEATURE:
<223> OTHER INFORMATION: vector encoding the protein sequence

<400> SEQUENCE: 9

```
gacattgtga tgtcacagtc tccatcctcc ctagctgtgt cagttggaga aaggttact       60 atgagctgca agtccagtca gagccttta tatagtagca atcaaaagaa ctacttggcc     120
tggtaccagc agaaaccagg gcagtctcct aaactgctga tttactgggc atccactagg     180
gaatctgggg tccctgatcg cttcacaggc agtggatctg ggacagattt cactctcacc     240
atcagcagtg tgaaggctga agacctggca ctttattact gtcagcaata ttatagctat     300
ccgtacacgt tcggaggggg gaccaagctg gaaataaaa                             339
```

<210> SEQ ID NO 10
<211> LENGTH: 115
<212> TYPE: PRT
<213> ORGANISM: Artificial Sequence

```
<220> FEATURE:
<223> OTHER INFORMATION: mAb

<400> SEQUENCE: 10

Glu Val Gln Leu Val Glu Ser Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Asp Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Arg Ser Glu Asp Thr Ala Met Tyr Tyr Cys
                85                  90                  95

Ala Arg Arg Asn His Phe Thr Tyr Trp Gly Gln Gly Thr Leu Val Thr
            100                 105                 110

Val Ser Ala
        115

<210> SEQ ID NO 11
<211> LENGTH: 107
<212> TYPE: PRT
<213> ORGANISM: Artificial Sequence
<220> FEATURE:
<223> OTHER INFORMATION: mAb

<400> SEQUENCE: 11

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Val Thr Ser
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Tyr Pro Leu
                85                  90                  95

Thr Phe Gly Ala Gly Thr Lys Leu Glu Leu Lys
            100                 105

<210> SEQ ID NO 12
<211> LENGTH: 8
<212> TYPE: PRT
<213> ORGANISM: Artificial Sequence
<220> FEATURE:
<223> OTHER INFORMATION: mAb

<400> SEQUENCE: 12

Gly Phe Ser Phe Ser Ser Tyr Ala
1               5

<210> SEQ ID NO 13
<211> LENGTH: 8
<212> TYPE: PRT
<213> ORGANISM: Artificial Sequence
<220> FEATURE:
```

<223> OTHER INFORMATION: mAb

<400> SEQUENCE: 13

Ile Ser Ser Gly Gly Asp Tyr Thr
1               5

<210> SEQ ID NO 14
<211> LENGTH: 8
<212> TYPE: PRT
<213> ORGANISM: Artificial Sequence
<220> FEATURE:
<223> OTHER INFORMATION: mAb

<400> SEQUENCE: 14

Ala Arg Arg Asn His Phe Thr Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: mAb

<400> SEQUENCE: 15

Gln Asp Val Val Thr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: mAb

<400> SEQUENCE: 16

Gln Gln Tyr Ser Ser Tyr Pro Leu Thr
1               5

<210> SEQ ID NO 17
<211> LENGTH: 345
<212> TYPE: DNA
<213> ORGANISM: Artificial Sequence
<220> FEATURE:
<223> OTHER INFORMATION: mAb DNA sequence

<400> SEQUENCE: 17

```
gaagtgcagc tggtggagtc tgggggaggc ttagtgaagc ctggagggtc cctgaaactc        60
tcctgtgcag cctctggatt ctctttcagt agctatgcca tgtcttgggt tcgccagact       120
ccggagaaga ggctggagtg ggtcgcaacc attagtagtg gtggtgatta cacctactat       180
ccagacagtg tgaagggtcg attcaccatc tccagagaca atgccaagaa caccctgtac       240
ctgcaaatga ccagtctgag gtctgaggac acggccatgt attactgtgc aagacgaaat       300
cattttactt actggggcca aggactctg gtcactgtct ctgca                        345
```

<210> SEQ ID NO 18
<211> LENGTH: 321
<212> TYPE: DNA
<213> ORGANISM: Artificial Sequence
<220> FEATURE:
<223> OTHER INFORMATION: mAb DNA sequence

<400> SEQUENCE: 18

```
gacattgtga tgacccagtc tcacaaattc atgtccacat cagtaggaga cagggtcagc        60
```

-continued

```
atcacctgca aggccagtca ggatgtggtt acttctgttg cctggtatca acagaaacca      120
gggcaatctc ctaaactact gatttactgg acatccaccc ggcacactgg agtccctgat      180
cgcttcacag gcagtggatc tgggacagat ttcactctca ccattagcaa tgtgcagtct      240
gaagacttgg cagattattt ctgtcagcaa tatagcagct atccgctcac gttcggtgct      300
gggaccaagc tggagctgaa a                                                321
```